United States Patent
Lee et al.

(10) Patent No.: US 8,057,959 B2
(45) Date of Patent: Nov. 15, 2011

(54) ADDITIVE OF ELECTRODE FOR FUEL CELL, ELECTRODE FOR FUEL CELL INCLUDING THE SAME, MANUFACTURING METHOD THEREOF, AND FUEL CELL USING THE SAME

(75) Inventors: Myung-jin Lee, Seoul (KR); Suk-gi Hong, Suwon-si (KR); Myung-dong Cho, Hwaseong-si (KR)

(73) Assignee: Samsung SDI Co., Ltd., Suwon-si, Gyeonggi-do (KR)

( * ) Notice: Subject to any disclaimer, the term of this patent is extended or adjusted under 35 U.S.C. 154(b) by 492 days.

(21) Appl. No.: 11/850,919

(22) Filed: Sep. 6, 2007

(65) Prior Publication Data

US 2008/0118817 A1    May 22, 2008

(30) Foreign Application Priority Data

Nov. 22, 2006 (KR) .................. 10-2006-0116041

(51) Int. Cl.
  *H01M 4/02* (2006.01)
(52) U.S. Cl. .......... 429/523; 429/530; 560/129; 562/11; 562/20; 562/8
(58) Field of Classification Search .............. 429/523, 429/530; 560/129; 562/11, 20, 8
See application file for complete search history.

(56) References Cited

U.S. PATENT DOCUMENTS

| | | | |
|---|---|---|---|
| 6,767,664 B2 * | 7/2004 | Akita et al. | 429/492 |
| 6,828,407 B2 * | 12/2004 | Sasaki et al. | 528/86 |
| 2002/0192535 A1 * | 12/2002 | Fukuda et al. | 429/42 |
| 2005/0244696 A1 * | 11/2005 | Kuromatsu et al. | 429/33 |
| 2006/0033226 A1 | 2/2006 | Wang | |
| 2007/0134530 A1 * | 6/2007 | Nakamura et al. | 429/30 |

* cited by examiner

*Primary Examiner* — Melvin Mayes
*Assistant Examiner* — Melissa Stalder
(74) *Attorney, Agent, or Firm* — Lee & Morse, P.C.

(57) ABSTRACT

Provided are an additive to an electrode for a fuel cell that is a proton conductive compound having at least one phosphate group, an electrode for a fuel cell including the same, a method of manufacturing the electrode for a fuel cell, and a fuel cell using the electrode. The additive to an electrode for a fuel cell improves the durability of a fuel cell and reduces the amount of phosphoric acid discharged during operation of the fuel cell by fixing the phosphoric acid. Accordingly, a fuel cell having improved efficiency may be prepared using the additive because of improved proton conductivity and durability.

16 Claims, 3 Drawing Sheets

ADDITIVE OF ELECTRODE FOR FUEL CELL, ELECTRODE FOR FUEL CELL INCLUDING THE SAME, MANUFACTURING METHOD THEREOF, AND FUEL CELL USING THE SAME

CROSS-REFERENCE TO RELATED APPLICATIONS

This application claims the benefit of Korean Application No. 2006-116041, filed Nov. 22, 2006, in the Korean Intellectual Property Office, the disclosure of which is incorporated herein by reference.

BACKGROUND OF THE INVENTION

1. Field of the Invention

Aspects of the present invention relate to an additive to electrodes for a fuel cell, an electrode for a fuel cell including the same, a method of manufacturing the electrode for a fuel cell, and a fuel cell using the electrode. More particularly, aspects of the present invention relate to an additive demonstrating improved phosphoric acid retention capacity, high temperature stability, and proton conductivity, as well as an electrode for a fuel cell including the additive, a method of manufacturing the electrode for a fuel cell, and a fuel cell using the electrode.

2. Description of the Related Art

Proton conductors that have excellent proton conductivity at a temperature in the range of 100-300° C. and are stable during long-term use in that temperature range are required in a fuel cell for power generation efficiency, system efficiency, and long-term durability of the components.

In a solid polymer electrolyte membrane fuel cell that uses phosphoric acid as a proton conductor, a sufficient amount of phosphoric acid needs to be supplied as a proton conducting medium for the high proton conductivity needed to promote the electrochemical reactions occurring in the electrodes. For this purpose, an additional process of doping with phosphoric acid is needed.

The added phosphoric acid flows within the electrode or is transferred through the electrolyte during the operation of the fuel cell, and flows from the fuel cell along with the water that is generated.

However, the phosphoric acid forms polyphosphoric acid at a fuel cell operating temperature in the range of 150-300° C. At this high temperature range, the generated polyphosphoric acid lowers the chemical stability of the electrolyte membrane. Thus, gaseous reactants may permeate through the electrolyte membrane and the open circuit voltage of the fuel cell may be reduced. As a result, the efficiency of the fuel cell may decrease.

A method of preparing an electrode material using an amine as a polymer forming precursor is disclosed in U.S. Patent Application Publication No. 2006-0033226.

SUMMARY OF THE INVENTION

Aspects of the present invention provide an additive to an electrode for a fuel cell where the additive demonstrates improved phosphoric acid retention capacity, high temperature stability, and proton conductivity, as well as an electrode for a fuel cell incorporating the additive that has improved proton conductivity and durability, and a method of preparing the electrode for a fuel cell. Aspects of the present invention also provide a fuel cell incorporating the electrode that has improved efficiency.

One aspect of the present invention provides an additive to an electrode for a fuel cell that is a proton conductive compound having at least one phosphoric acid group, where the proton conductive compound is selected from the group consisting of Formulae 1 to 5 or a polymerization product of a compound represented by Formula 6.

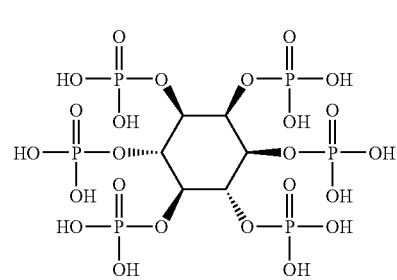

Formula 1

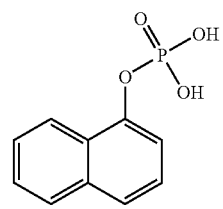

Formula 2

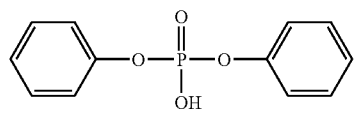

Formula 3

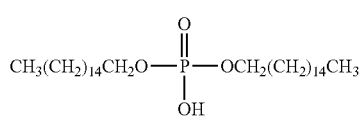

Formula 4

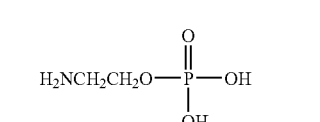

Formula 5

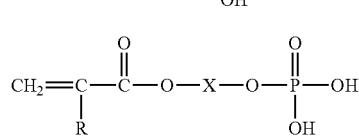

Formula 6

Here, X is a substituted or unsubstituted C1-C20 alkylene group and R is a hydrogen atom or a methyl group.

Another aspect of the present invention provides an electrode for a fuel cell that incorporates the additive, as well as a binder and a catalyst.

Another aspect of the present invention provides a method of preparing an electrode for a fuel cell, the method including: preparing a composition for forming an electrode catalyst layer by mixing the additive to an electrode for a fuel cell with a binder, a catalyst and a solvent; and then forming an electrode by coating the composition on a carbon support and heat treating the coated composition.

Another aspect of the present invention provides a fuel cell including a cathode, an anode, and an electrolyte membrane interposed between the cathode and the anode, wherein at least one of the cathode and anode includes the additive to an electrode for a fuel cell, as well as a binder and a catalyst.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become more apparent and more readily appreciated from the following description of the embodiments, taken in conjunction with the accompanying drawings of which.

DETAILED DESCRIPTION OF THE EMBODIMENTS

Figure 1:
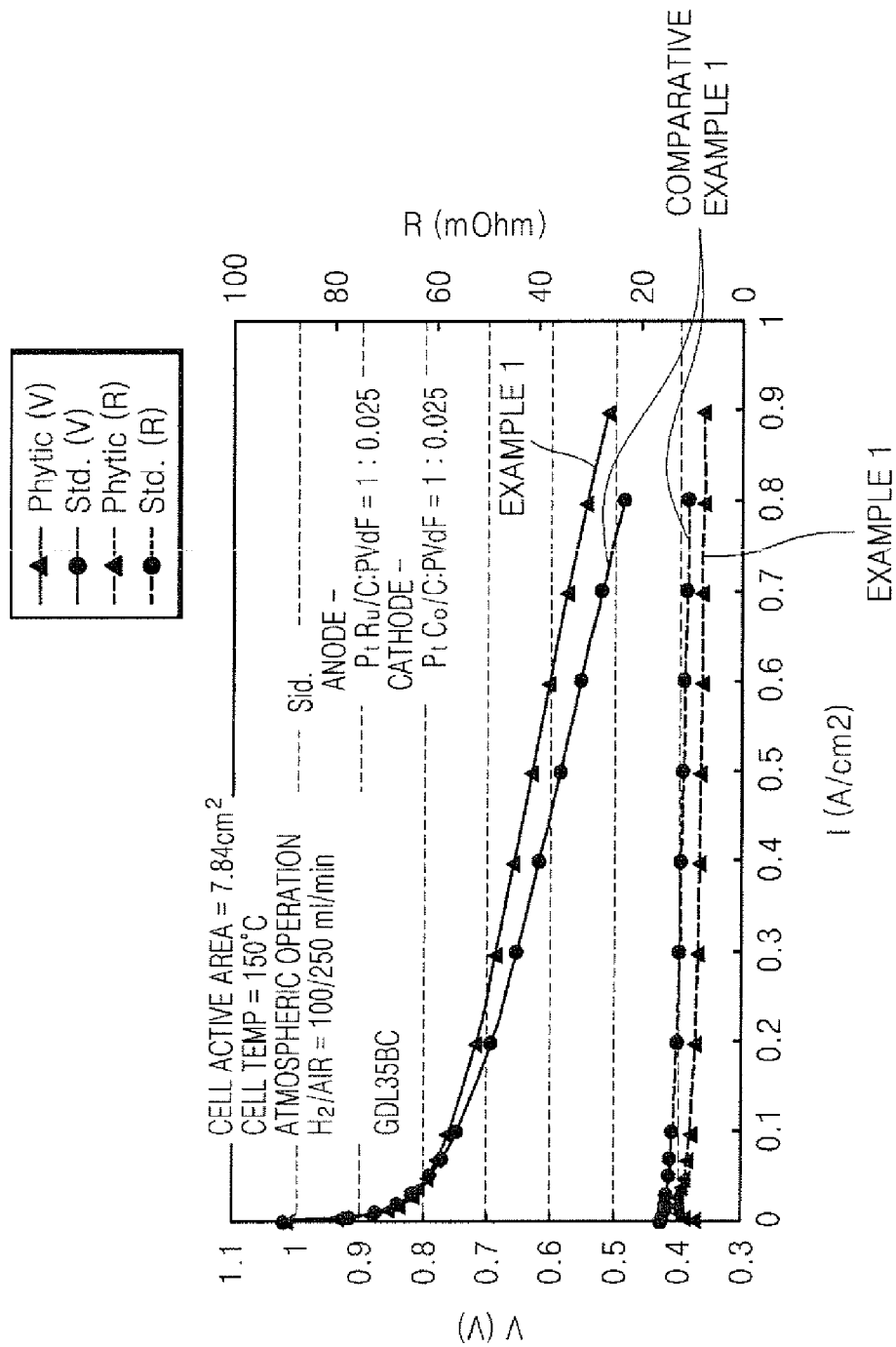
FIG. 1 is a graph illustrating voltages of fuel cells prepared according to Example 1 and Comparative Example 1 as a function of current densities.

Reference will now be made in detail to the present embodiments of the present invention, examples of which are illustrated in the accompanying drawings. The embodiments are described below in order to explain the present invention by referring to the figures.

The additive to an electrode for a fuel cell according to an embodiment of the present invention is a proton conductive compound including phosphoric acid groups, preferably an organophosphate or a proton conductive polymer with multiple phosphoric acid groups, a high boiling point or low vapor pressure and a high viscosity or low fluidity.

The organophosphate may be represented by Formulae 1 to 5.

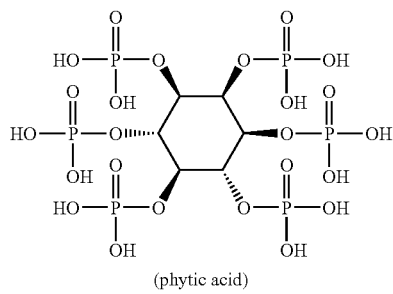
(phytic acid) — Formula 1

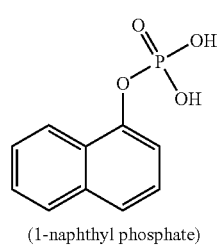
(1-naphthyl phosphate) — Formula 2

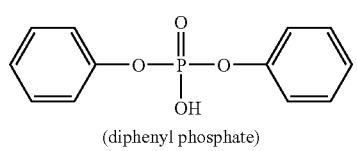
(diphenyl phosphate) — Formula 3

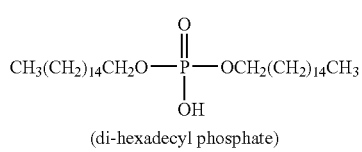
(di-hexadecyl phosphate) — Formula 4

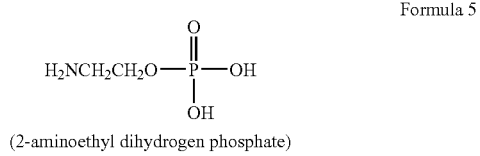
(2-aminoethyl dihydrogen phosphate) — Formula 5

Examples of the proton conductive polymer may include the polymerization product of a compound represented by Formula 6. The proton conductive polymer may form a membrane with a binder when the electrode is formed.

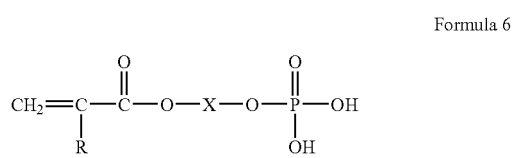
Formula 6

Here, X is a substituted or unsubstituted C1-C20 alkylene group and R is a hydrogen atom or a methyl group. In this invention, alkylene means a divalent saturated group such as —$CH_2$— or —$CH_2CH_2$—.

The polymerization product of the compound of Formula 6 has an average molecular weight from 100 to 1000, and it is obtained by a cross-linking reaction of the compound represented by Formula 6. The cross linking is performed using thermal polymerization.

Examples of the compound of Formula 6 may include a compound represented by Formulae 7 and 8.

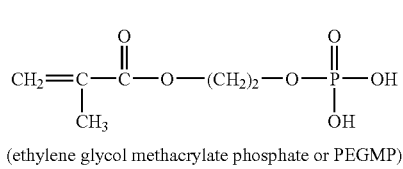
(ethylene glycol methacrylate phosphate or PEGMP) — Formula 7

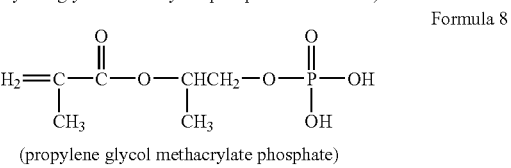
(propylene glycol methacrylate phosphate) — Formula 8

The additive to an electrode for a fuel cell according to the current embodiment improves the durability of a fuel cell and reduces the discharged amount of phosphoric acid by fixing the phosphoric acid in the electrode. Accordingly, the fuel cell efficiency is improved because of the improved proton conductivity of the electrode, and the durability of the electrolyte membrane is improved by replacing phosphoric acid dopant with the compounds of the invention.

Higher proton conductivity can be obtained using a smaller amount of phosphoric acid compared to a conventional electrode for a fuel cell. For example, it is noted that phytic acid (Formula 1) has 6 phosphoric acid groups per molecule. The amount of phytic acid used as an additive in the electrode slurry preparation of the current embodiment (described below) was calculated. The amount of the phytic acid added to the electrode was 0.3523 mg phytic acid/cm$^2$. The electrode has better efficiency with far less of a doped amount (2~5%) compared to a conventional phosphoric acid doped ABPBI cathode (17.5 mg of phosphoric acid/cm$^2$).

A method of preparing an electrode for a fuel cell according to an embodiment of the present invention will now be described. First, a composition for forming an electrode catalyst layer is prepared by mixing the additive to an electrode, a catalyst, a binder and a solvent. Then, an electrode was formed by coating the composition on a carbon support and heat treating the coated composition.

The amount of the additive may be in the range of 3-50 parts by weight based on 100 parts by weight of the catalyst. When the amount of the additive is less than 3 parts by weight, the beneficial effect of adding the additive is not sufficient. On the other hand, when the amount of the additive is greater than 50 parts by weight, the relative loading amount of the catalyst may decrease.

Platinum may be used as the catalyst, or an alloy or a mixture of platinum and at least one metal selected from the group consisting of gold, palladium, rhodium, iridium, ruthenium, tin, molybdenum, cobalt, and chromium may be used as the catalyst.

The binder may include at least one polymer selected from the group consisting of poly(vinylidenefluoride), polytetrafluoroethylene, a tetrafluoroethylene-hexafluoropropylene copolymer and. The amount of the binder may be in the range of 1-50 parts by weight based on 100 parts by weight of the catalyst. When the amount of the binder is less than 1 part by weight, the wetting condition of phosphoric acid in the electrode may not be sufficiently improved. On the other hand, when the amount of the binder is greater than 50 parts by weight, flooding of the fuel may be accelerated.

The solvent may be N-methylpyrrolidone (NMP), dimethylacetamide (DMAc), or the like, and the amount of the solvent may be in the range of 300-600 parts by weight based on 100 parts by weight of the catalyst. When the amount of the solvent is out of the range described above, the electrode formation operation may not be easily performed.

The carbon support is fixed on a glass substrate to facilitate coating. The coating may be performed using a doctor blade, bar coating, screen printing, or the like, but the coating method is not limited thereto.

The composition is coated and heat treated to evaporate the solvent at a temperature in the range of 80-180° C. The composition may be heat treated for 10-60 minutes, but the heat treatment time may vary according to the heat treatment temperature. For example, the composition may be heat treated at 80° C. for 1 hour or longer, at 120° C. for 30 minutes or longer, and at 150° C. for 10 minutes or longer.

An electrode prepared according to the method described above includes a catalyst, a binder, and an additive.

The electrolyte membrane may be any electrolyte membrane that is commonly used in a fuel cell. For example, a polybenzimidazole electrolyte membrane, a polybenzoxazine-polybenzimidazole copolymer electrolyte membrane, and a polytetrafluoroethylene porous membrane may be used.

The support may be carbon paper, preferably water repellent carbon paper, and more preferably water repellent carbon paper to which a water repellent carbon black layer is applied or carbon cloth.

The water repellent carbon paper includes about 5-50 wt % of a hydrophobic polymer such as polytetrafluoroethylene (PTFE), and the hydrophobic polymer may be sintered. A gas diffusion layer is treated to be water repellent to ensure the entry/exit path of both the polar liquid reactant and the gaseous reactants.

In the water repellent carbon paper having the water repellent carbon black layer, the water repellent carbon black layer includes carbon black and about 20-50 wt % of the hydrophobic polymer, such as PTFE, as a hydrophobic binder. The water repellent carbon black layer is applied to a side of the water repellent carbon paper. The hydrophobic polymer in the water repellent carbon black layer is sintered.

Further, a fuel cell according to an embodiment of the present invention may include a cathode, an anode, and an electrolyte membrane interposed between the cathode and the anode, wherein at least one of the cathode and anode includes the additive to an electrode, a binder and a catalyst. The cathode and anode respectively include a catalyst layer and a diffusion layer.

The fuel cell of the current embodiment may be more practically used for home services. The fuel cell for home services may be prepared using a method that is commonly used in manufacturing a fuel cell, and thus the method will not be described in detail in the instant specification.

Aspects of the present invention will be described in greater detail with reference to the following examples. The following examples are for illustrative purposes and are not intended to limit the scope of the invention.

EXAMPLE 1

1.0 g of PtCo/C, 0.1 g of phytic acid represented by Formula 1, 0.018 g of polyvinylidene fluoride and 3.5 g of the solvent NMP were mixed and stirred at room temperature for 5 minutes to prepare a slurry that is used to form a cathode catalyst layer.

The slurry that is used to form the cathode catalyst layer was coated using bar coating on carbon paper as a carbon support, and different samples of the coated slurry were dried at 80° C. for 1 hour, at 120° C. for 30 minutes, and at 150° C. for 10 minutes to prepare a cathode.

1.0 g of PtRu/C, 0.1 g of phytic acid represented by Formula 1, 0.018 g of polyvinylidene fluoride and 3.5 g of the solvent NMP were mixed and stirred at room temperature for 5 minutes to prepare a slurry that is used to form an anode catalyst layer.

The slurry that is used to form the anode catalyst layer was coated using bar coating on carbon paper as a carbon support, and different samples of the coated slurry were dried at 80° C. for 1 hour, at 120° C. for 30 minutes, and at 150° C. for 10 minutes to prepare an anode.

NAFION® (DuPont Company) 115 was used as an electrolyte membrane, and interposed between the cathode and the anode to prepare a fuel cell. The operating temperature of the fuel cell was 150° C. Air was supplied to the cathode at 250 ml/min and hydrogen was supplied to the anode at 100 ml/min.

EXAMPLE 2

A cathode, an anode and a fuel cell were prepared in the same manner as in Example 1, except that 0.05 g of PEGMP represented by Formula 7 was used instead of the phytic acid represented by Formula 1 to prepare the slurries that are used to form the anode and cathode catalyst layers. The amount of catalyst (PtCo) loading in the cathode was 1.91 mg/cm$^2$, and the amount of catalyst (PtRu) loading in the anode was 1.22 mg/cm$^2$.

NAFION® 115 was used as an electrolyte membrane. The operating temperature of the fuel cell was 150° C. under non-humidifying (dry) conditions. Air was supplied to the cathode at 250 ml/min and hydrogen was supplied to the anode at 100 ml/min.

COMPARATIVE EXAMPLE 1

Electrodes were prepared in the same manner as in Example 1, except that phytic acid was not used to make the slurries that are used to form the anode and cathode catalyst layers.

COMPARATIVE EXAMPLE 2

Electrodes were prepared in the same manner as in Example 1, except that 0.1 g of 3,3'-diaminobenzidine (DAB) was used instead of phytic acid to make the slurries that are used to form the anode and cathode catalyst layers.

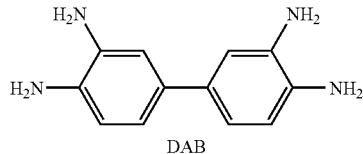

DAB

Figure 2:
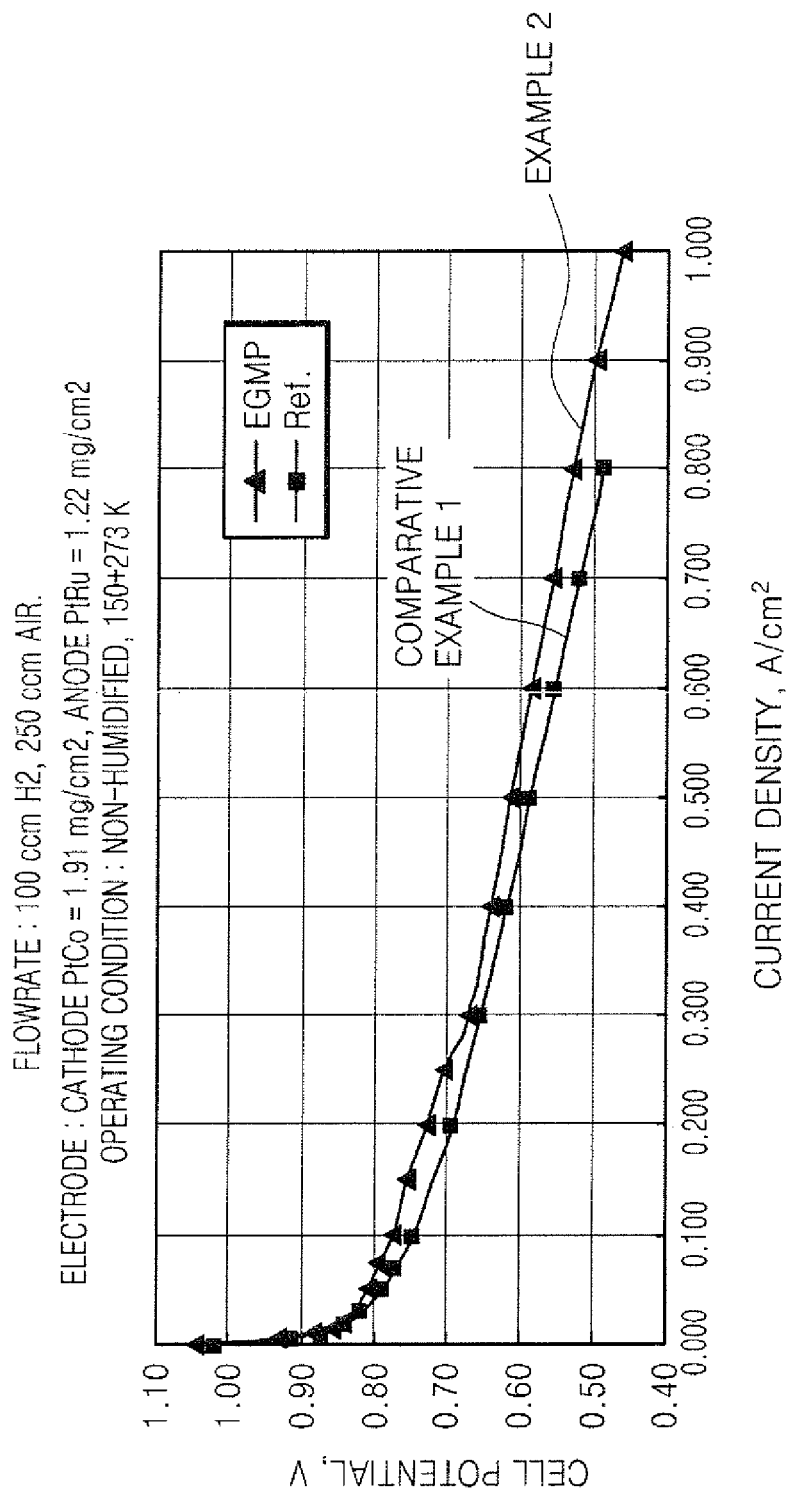
FIG. 2 is a graph illustrating voltages of fuel cells prepared according to Example 2 and Comparative Example 1 as a function of current densities.

Voltages of the fuel cells prepared according to Examples 1-2 and Comparative Example 1 were measured as a function of current densities, and the results are shown in FIGS. 1 and 2. Further, voltages of the fuel cells prepared according to Comparative Examples 1 and 2 were measured as a function of current densities, and the results are shown in FIG. 3.

Figure 3:
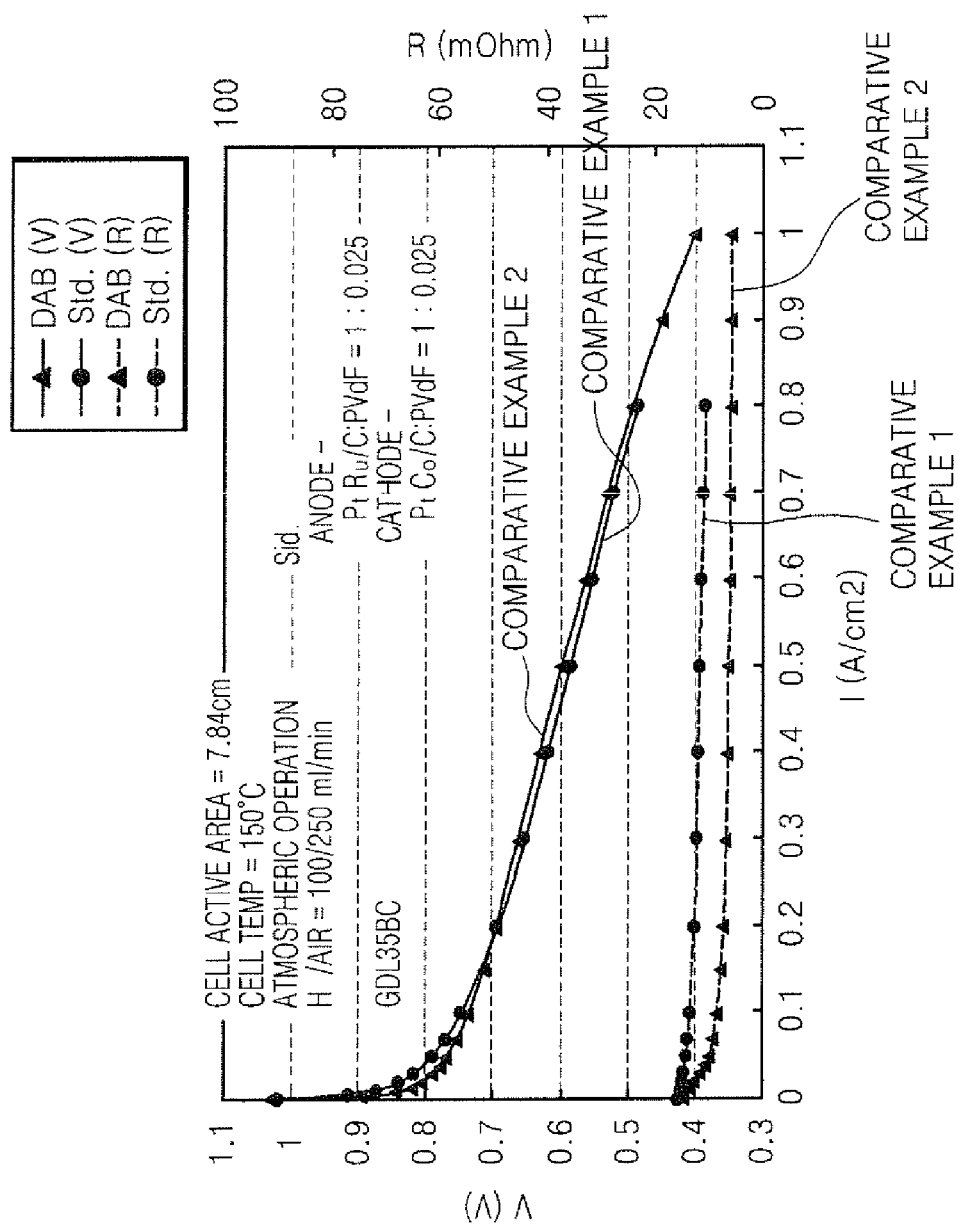
FIG. 3 is a graph illustrating voltages of fuel cells prepared according to Comparative Examples 1 and 2 as a function of current densities.

Referring to FIGS. 1 to 3, the electrode efficiency of the fuel cells to which the additive to an electrode of Examples 1 and 2 was added was improved compared to the fuel cell of Comparative Example 1 to which the additive was not added and the fuel cell of Comparative Example 2 to which an amine additive was added.

The additive to an electrode for a fuel cell of the present invention improves the durability of a fuel cell and reduces the amount of phosphoric acid discharged during operation of the fuel cell by fixing the phosphoric acid. Accordingly, a fuel cell having improved efficiency may be prepared using the additive because of improved proton conductivity and durability of the fuel cell.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An electrode for a fuel cell comprising a mixture of an additive, a binder, and a catalyst, wherein:
    the additive in the mixture of the electrode is a proton conductive compound including at least one phosphoric acid group, and
    the proton conductive compound is one selected from the group consisting of Formulae 1, 4 and 5:

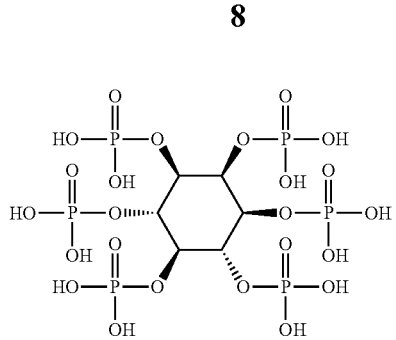

Formula 1

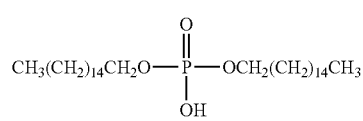

Formula 4

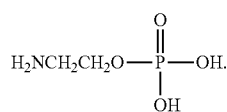

Formula 5

2. The electrode for a fuel cell of claim 1, wherein the concentration of the additive in the mixture of the electrode is in the range of 3-50 parts by weight based on 100 parts by weight of the catalyst.

3. The electrode for a fuel cell of claim 1, wherein the binder is at least one polymer selected from the group consisting of poly(vinylidene fluoride), polytetrafluoroethylene, and a tetrafluoroethylene-hexafluoropropylene copolymer.

4. The electrode for a fuel cell of claim 3, wherein the binder concentration is in the range of 1-50 parts based upon 100 parts by weight of the catalyst.

5. The electrode for a fuel cell of claim 1, wherein the catalyst is platinum or an alloy or mixture of platinum and at least one metal selected from the group consisting of gold, palladium, rhodium, iridium, ruthenium, tin, molybdenum, cobalt and chromium.

6. The electrode for a fuel cell of claim 1, wherein the electrode is composed of the mixture of the proton conductive compound, the binder, and the catalyst, such that the proton conductive compound is fixed within the electrode with the binder and the catalyst.

7. The electrode for a fuel cell of claim 1, wherein the additive is the compound of Formula 1:

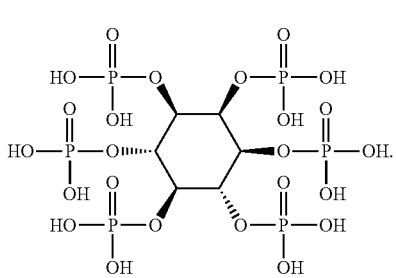

Formula 1

8. A method of preparing an electrode for a fuel cell, the method comprising:
    providing a composition for forming an electrode catalyst layer, the composition including a mixture of an additive for an electrode, a binder, a catalyst, and a solvent; and
    forming an electrode including the additive, the binder, and the catalyst by coating the composition on a carbon support and heat treating the coated composition, wherein the additive is a proton conductive compound including at least one phosphoric acid group and the proton conductive compound is one selected from the group consisting of Formulae 1, 4 and 5:

Formula 1

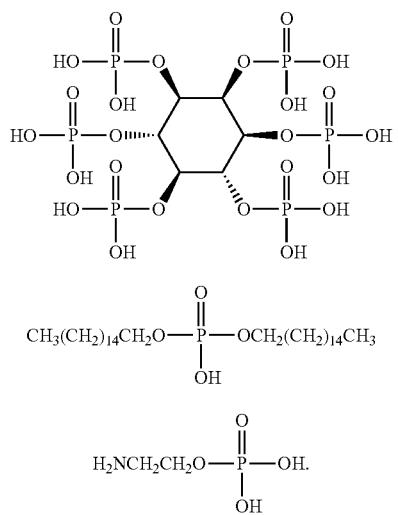

Formula 4

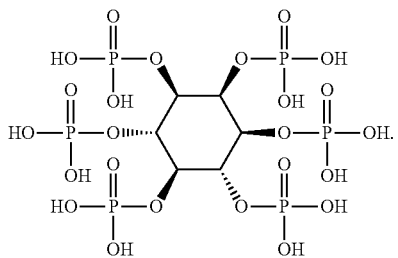

Formula 5

$$H_2NCH_2CH_2O-\overset{\overset{O}{\|}}{\underset{\underset{OH}{|}}{P}}-OH.$$

9. The method of claim 8, wherein forming the electrode includes fixing the proton conductive compound within the electrode by mixing the composition of the proton conductive compound, the binder, the catalyst, and the solvent together before coating the composition on the carbon support.

10. The method of claim 8, wherein the additive is the compound of Formula 1:

Formula 1

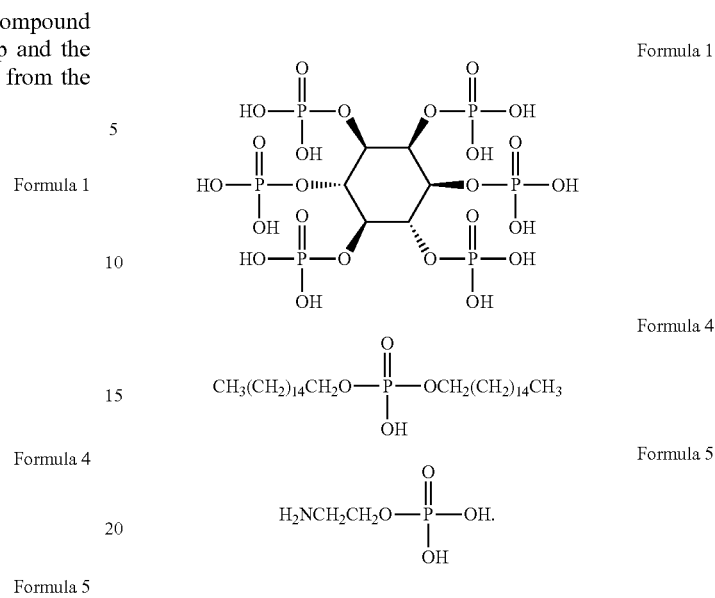

11. A fuel cell comprising a cathode, an anode, and an electrolyte membrane interposed between the cathode and the anode, wherein:
   at least one of the cathode and anode includes a mixture of an additive to an electrode, a binder, and a catalyst therein, and
   the additive in the mixture is a proton conductive compound including at least one phosphoric acid group and the proton conductive compound is one selected from the group consisting of Formulae 1, 4 and 5:

Formula 1

Formula 4

$$CH_3(CH_2)_{14}CH_2O-\overset{\overset{O}{\|}}{\underset{\underset{OH}{|}}{P}}-OCH_2(CH_2)_{14}CH_3$$

Formula 5

$$H_2NCH_2CH_2O-\overset{\overset{O}{\|}}{\underset{\underset{OH}{|}}{P}}-OH.$$

12. The fuel cell of claim 11, wherein the amount of the additive in the mixture for the least one of the cathode and anode is in the range of 3-50 parts by weight based on 100 parts by weight of the catalyst.

13. The fuel cell of claim 11, wherein the electrolyte membrane is selected from the group consisting of a polybenzimidazole electrolyte membrane, a polybenzoxazine-polybenzimidazole copolymer electrolyte membrane and a polytetrafluoroethylene porous membrane.

14. The fuel cell of claim 11, wherein the electrolyte membrane is disposed directly on the mixture of the additive to the electrode, the binder, and the catalyst of the at least one of the cathode and anode.

15. The fuel cell of claim 14, wherein the at least one of the cathode and anode is composed of the mixture of the proton conductive compound, the binder, and the catalyst, such that the proton conductive compound is fixed within the at least one of the cathode and the anode with the binder and the catalyst.

16. The fuel cell of claim 11, wherein the additive is the compound of Formula 1:

Formula 1

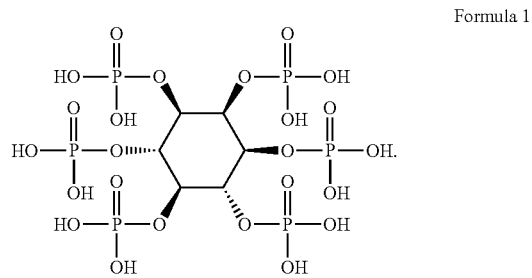

* * * * *